United States Patent [19]

Brown

[11] Patent Number: 5,043,479
[45] Date of Patent: * Aug. 27, 1991

[54] CHEMICALLY AND OPTICALLY PURE DIISOPINOCAMPHEYLHALOBORANES

[75] Inventor: Herbert C. Brown, West Lafayette, Ind.

[73] Assignee: Aldrich Chemical Company, Inc., Milwaukee, Wis.

[*] Notice: The portion of the term of this patent subsequent to Sep. 20, 2005 has been disclaimed.

[21] Appl. No.: 402,132

[22] Filed: Sep. 1, 1989

Related U.S. Application Data

[63] Continuation of Ser. No. 241,967, Sep. 8, 1988, abandoned, which is a continuation-in-part of Ser. No. 902,175, Aug. 29, 1986, Pat. No. 6,772,752.

[51] Int. Cl.$^5$ .................................................. C07F 5/02
[52] U.S. Cl. ............................................................ 568/6
[58] Field of Search ............................................. 568/6

[56] References Cited

U.S. PATENT DOCUMENTS 4,713,380 12/1982 Brown .............................. 568/6 X
4,772,752 9/1988 Brown .................................. 568/6

OTHER PUBLICATIONS

Brown, "J.A.C.S.", 105, pp. 2092–2093 (1983).

Primary Examiner—Paul F. Shaver
Attorney, Agent, or Firm—Joyce R. Niblack; Robert L. Niblack

[57] ABSTRACT

Novel chemically pure diisopinocampheylhaloboranes of essentially 100% ee, represented by the formula $Ipc_2BX$ wherein Ipc is isopinocampheyl and X is halo.

5 Claims, No Drawings

CHEMICALLY AND OPTICALLY PURE DIISOPINOCAMPHEYLHALOBORANES

CROSS-REFERENCE TO RELATED APPLICATIONS

This is a continuation of application Ser. No. 07/241,967, filed Sept. 8, 1988, now abandoned, which was a continuation-in-part of Ser. No. 902,175, filed Aug. 29, 1986, now U.S. Pat. No. 4,772,752.

BACKGROUND OF THE INVENTION

The reduction of prochiral ketones produces an alcohol which contains an asymmetric carbon atom, designated by the asterik in the following reaction.

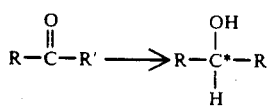

Considerable effort has been expended in the past and continues to be expended in finding asymmetric reducing agents which will achieve the reduction of such carbonyl groups to give optically active alcohols of high optical purity (100% optical purity = 100% ee).

One valuable reagent is B-isopinocampheyl-9-borabicyclo[3.3.1]nonane, B-Ipc-9-BBN, made by hydroborating optically active α-pinene with 9-borabicyclo[3.3.1]nonane (9-BBN) and sold by Aldrich Chemical Company under the registered trademark Alpine-Borane, and the modified borohydride reagent, NB-Enantride [M. M. Midland, A. Kazubski, *J. Org. Chem.*, 47, 2495 (1982).

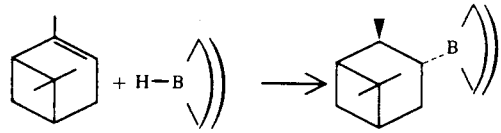

This reagent readily reacts with deuteroaldehydes, RCDO, to give the reduced product, a primary alcohol, in optical purities approaching 100% [M. M. Midland, S. Greer, A. Tramontano, S. A. Zderic, *J. A. Chem. Soc.*, 47, 2352 (1979)].

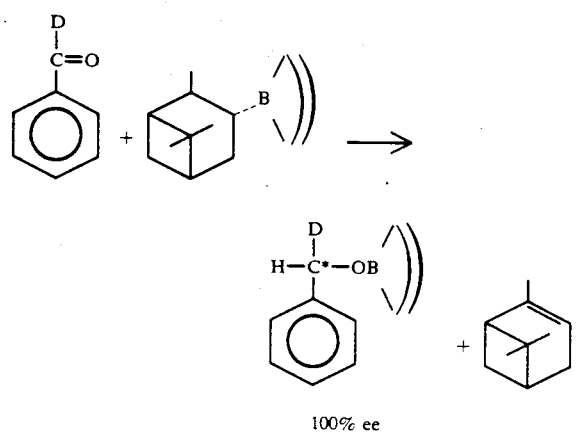

The α-pinene can be recovered and reused.
Originally, this reagent gave very poor results in the reduction of ketones. [A. Tramontano, Ph.D. Thesis, U. Cal. Riverside, (1980)], resulting in end product of only 7% optical purity.

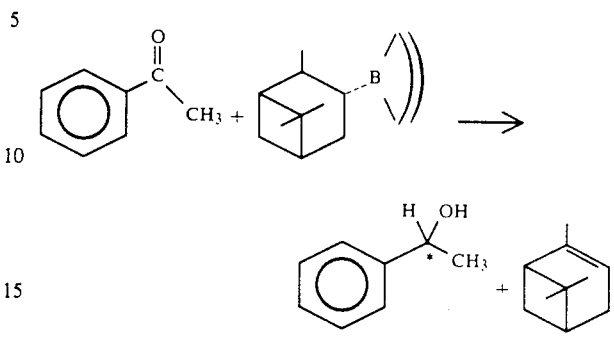

However, it does reduce acetylenic ketones in high optical purity [M. M. Midland, A. Tramontano, A. Kazubski, R. S. Graham, D. S. Tsai, D. B. Cardin, *Tetrahedron*, 40, 1371 (1984)].

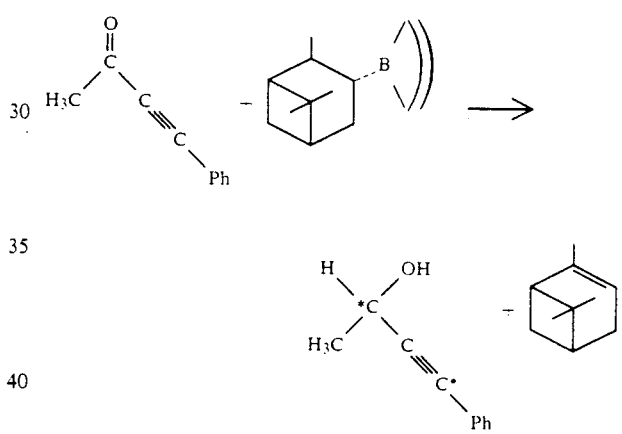

Another modified borohydride reagent, K 9-O-DIPGF-9-BBNH is highly promising. [H. C. Brown, W. S. Park and B. T. Cho, *J. Org. Chem.*, 51, 1934 (1986).]

In addition, an enzymatic chiral reduction of ketones was recently reported by E. Keinan, E. K. Hafeli, K. K. Seth and R. Lamed, *J. Am. Chem. Soc.*, 108, 162 (1986).

It still remains highly desirable to find a reagent that will do equally well in reducing aliphatic, alicyclic, and aromatic ketones. Indeed, it was discovered that carrying out the reaction under neat conditions or concentrated solutions provided product having 87% optical purity. [H. C. Brown and G. C. Pai, *J. Org. Chem.*, 50, 1384 (1985).]

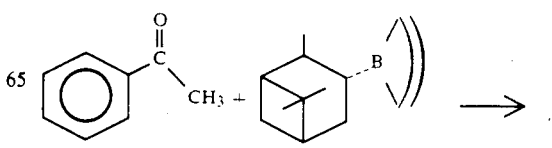

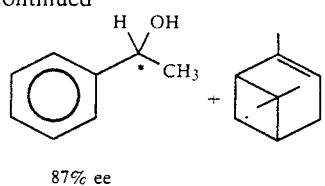

87% ee

Even better results (94% optical purity) can be realized by carrying out the reduction under exceptionally high pressures, 6000 atmos. [M. M. Midland and J. I. McLoughlin, J. Org. Chem., 49 1317 (1984)].

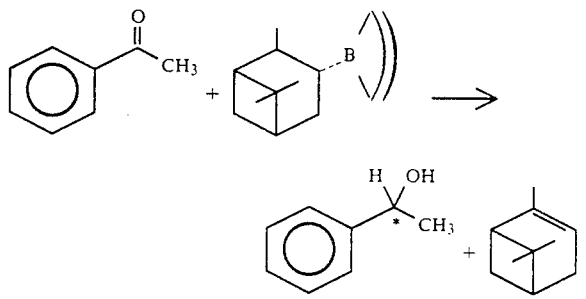

In 1 983, I reported the preparation of diisopinocampheylchloroborane via hydroboration of (+)-α-pinene (91.3% ee) with monochloroborane etherate ($H_2BCl \cdot OEt_2$) in ethyl ether at 0° C. Herbert C. Brown et J. Am. Chem. Soc. 1983, 105, 2092-2093. The intermediate diisopinochloroborane was not isolated at that time, and it was subsequently discovered that the reaction described in that publication does not yield a pure, recrystallizable product. Rather than $Ipc_2BCl$, mixtures of optical isomers of $Ipc_2BCl$, $IpcBCl_2$ and $Ipc_2BH$ were obtained. It was impossible to crystallize chemically pure $Ipc_2BCl$ from this mixture, and the mixture itself, which had an average optical purity of approximately 91.3% ee, was unsatisfactory for achieving asymmetric reduction of ketones in high enantiomeric excess. When the reduction of acetophenone using $Ipc_2BCl$ prepared via the 1983 procedure, the product alcohol was only approximately 80% ee.

Unisolated, uncharacterized $Ipc_2BCl$ was also reported by Uzarewicz, I. and Uzarewicz, A., Roczniki Chemii, 976, 50, 1351.

However, it was not until the advent of the present invention that it became possible to obtain chemically and optically pure diisopinocampheylhalohaloboranes, i.e., essentially 100% ee (enantiomeric excess). These valuable intermediates permit the preparation of alcohols of essentially 100% ee.

Thus, prior to the advent of the present invention, there remained a longstanding need for reagents which have an exceptional ability to achieve the reduction of many types of ketones in very high optical purities under very simple conditions. The present invention provides such reagents.

SUMMARY OF THE INVENTION

The present invention provides chemically pure diisopinocampheylhaloboranes of essentially 100% ee, represented by the formula:

$Ipc_2BX$ wherein Ipc is isopinocampheyl and X is halo.

The term "halo", as used herein, refers to chloro, fluoro, bromo and iodo.

The term "essentially 100% ee", as used herein, refers to an enantiomeric excess of at least 95% of one of the members of an enantiomeric pair. The term "optically pure" is synonomous.

The term "ee" is an abbreviation for "enatiomeric excess".

The term "enantiomeric pair" refers to a pair of substances whose molecules are nonidentical mirror images.

The compounds of this invention may also be represented by the formula

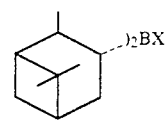

The optically active boron halides of the present invention are optically stable over reasonable periods of time. Moreover, some of them are exceptionally reactive reducing agents, reacting far faster with carbonyl compounds than 9-B-isopinocampheylbicyclo[3.3.1] nonane.

Generally speaking, the boron halides of this invention are prepared according to the following illustrative reaction schemes.

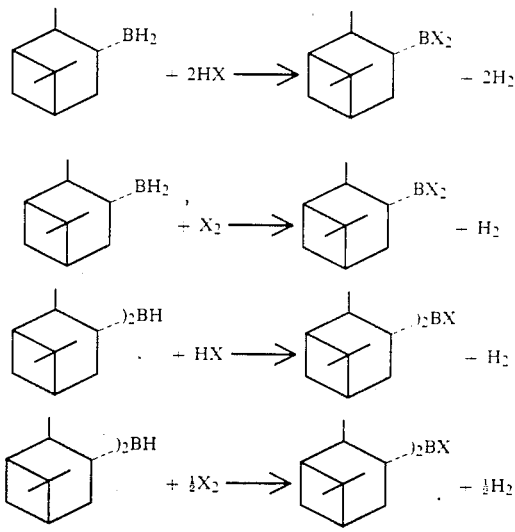

In general, the more active halogens, fluorine and chlorine, are best used as the hydrogen halide, HF and HCl. The least reactive halogen, iodine, is best used as the halogen. Bromine can be used in either form.

The presently preferred boron halide is diisopinocampheylchloroborane, a remarkably efficient chiral reducing agent for aromatic prochiral ketones (aralkyl and heteroaralkyl ketones) and α-tertiary alkyl ketones having superior optical purities than those obtained by prior art methods and reagents.

DETAILED DESCRIPTION OF PREFERRED EMBODIMENTS

The following examples further illustrate the present invention. All operations werer carried out under nitrogen. Unless otherwise indicated, optical rotations were measured at 20° C.

EXAMPLE 1

Preparation of Chemically and Optically Pure Diisocampheylchloroborane

Diisopinocampheylborane, prepared from (+)-α-pinene (230 mmol, 100% ee) and $BH_3.SMe_2$ (100 mmol) in tetrahydrofuran (THF) (96 mL) at 0° C. by the method of H. C. Brown et al, *J. Org. Chem.*, 47, 5065 (1982), was suspended in ethyl ether (50 mL) at −78° C. Dry hydrogen chloride in ethyl ether (1 equiv., calculated for the amount of $Ipc_2BH$) was added. After being stirred for 15 minutes at −78° C., the reaction mixture was warmed to 0° C. and stirred at that temperature until all of the solid dissolve and gas evolution ceased (2 h). $^{11}B$ NMR showed a single peak at δ76 ppm (relative to $BF_3.OEt_2$). Upon removal of the ether solvent and cooling, diisopinocampheylchloroborane solidified (mp 54°-56° C. after crystallization from pentane, >99% ee). The overall yield based on $BH_3.SMe_2$ is 75% $[α]_D$ −67.07° (c 13.5, $CH_2Cl_2$).

EXAMPLE 2

Preparation of Chemically and Optically Pure Diisopinocampheylbromoborane

Diisopinocampheylbromoborane was prepared in two ways. 1) By reacting $Ipc_2BH$ with HBr in ether and 2) by reacting $Ipc_2BH$ with $Br_2$ as follows.

1) HBr in ether was prepared by passing the gas from a lecture bottle through ice cold ether. The solution was standardized by titration with an aliquot with standard NaOH. To $Ipc_2BH$ (19.0 g, 66.5 mmol) cooled to −78° C. in a 250 mL round-bottom flask under a nitrogen atmosphere was added ether (50 mL), followed after 15 minutes by 21.38 mL of 3.11N HBr in ether. After stirring for another 15 min. at −78° C., the mixture was brought to 0° C. and stirred until all of the $Ipc_2BH$ dissolved. $^{11}B$ NMR showed a broad singlet at δ80.00 ($Ipc_2BBr$). Following methanolysis of an aliquot, the product showed a broad singlet at δ53.00 ($Ipc_2BOMe$). The ether was pumped off to obtain a white solid in a yield of 21.47 g (88%).

2) Diisopinocampheylborane was prepared in ether, crystallized out, the excess α-pinene and ether removed and the crystals washed with ice cold ether and dried under vacuum. (Preparation of $Ipc_2BH$ in THF leaves some THF occluded in the crystals which can be cleaved by $Ipc_2BBr$, causing the reagent to become impure.) To 25.96 g of $Ipc_2BH$ kept at −78° C. was added ~75 ml of $CH_2Cl_2$ freshly distilled over $P_2O_5$. To the cold suspension, $Br_2$ (6.26 g, 2.2 mL) in $CH_2Cl_2$ (10 mL) was added. After stirring for 15 min, the mixture was raised to 0° C. The solid $Icp_2BH$ dissolves within 1 h and the color of $Br_2$ disappears. $^{11}B$ NMR showed a broad singlet at δ80.00. Methanolysis of an aliquot gave a product which exhibited a broad singlet at δ53.00. The $CH_2Cl_2$ was pumped off to obtain a white solid: 31.66 g (100% yield, >99% ee), mp 58°-60° C., $[α]_D$ −54.68° (c 2.35, $CH_2Cl_2$).

EXAMPLE 3

Preparation of Monoisopinocampheyldichloroborane

To monoisopinocampheylborane in ethyl ether (78 mL of 0.64M, 50 mmol) in a 250 mL round-bottom flask was added HCl in ethyl ether (35.5 mL of 2.82N, 100 mmol) at ice salt temperature. There was a vigorous, immediate reaction with simultaneous evolution of hydrogen. $^{11}B$ NMR showed a peak at δ19.00 ppm, presumably due to an ether complex, $IpcBCl_2.OEt_2$. (Methanolysis shifts the peak to 32.00, presumably due to the formation of the boronic ester $IpcB(OMe)_2$.) The ether was pumped off at aspirator vacuum and the residue distilled at 52°-55°/0.1 mm. Frothing occurs while distilling. It is advisable to use a big flask and a distillation head with a long Vigreaux column. The product is obtained as a clear liquid, the ether-free compound, $IpcBCl_2$, >99% ee. The yield realized was 8.9 g, 81.3%. $^{11}B$ NMR neat and in $CH_2Cl_2$ showed a peak at δ63.00, $[α]_D$ −24.00 (c 7.62, $CH_2Cl_2$). Ether-free $IpcBCl_2$ is stable at room temperature for several months.

EXAMPLES 4-8

Following the methods of Examples 1-3 diisopinocampheylhaloboranes of essentially 100% ee set forth in Table 1 were prepared. The properties of the compounds prepared in Examples 1-3 are included.

TABLE 1

| Properties of Diisopinocampheylborohalides | |
| --- | --- |
| Compound | Properties |
| $Ipc_2BF$ | Colorless syrup. $^{11}B$ NMR δ 56.00 ppm, 80% Yield. >99% ee. |
| $Ipc_2BCl$ | Colorless crystals. mp 54-56° C. $^{11}B$ NMR δ76.0 ppm. $[α]_D$ = −67.07° (c 13.5, $CH_2Cl_2$). Stable in $CH_2Cl_2$, EE and THF. Pryophoric. Stable under nitrogen, stored at 0° C. 75% Yield. >99% ee. |
| $Ipc_2BBr$ | Colorless solid. mp 58-60° C. $^{11}B$ NMR δ80.00 ppm. $[α]_D$ −54.68 (c 2.25, $CH_2Cl_2$). Cleaves ether slowly and THF rapidly (2h). Pyrophoric. Stable when stored under nitrogen at 0° C. 88% Yield. >99% ee. |
| $Ipc_2BI$ | White solid, extremely hydroscopic. $^{11}B$ NMR δ 84.0 ppm. Stable in $CH_2Cl_2$. Cleaves ether slowly in 24 hours and reacts with THF instantaneously. Pyrophoric. Cannot be stored. 85% Yield. >99% ee. |

EXAMPLE 9

Reduction of 3,3-Dimethyl-2-butanone with $Ipc_2BCl$

An oven-dried 100 mL round-bottom flask equipped with a septum-capped sidearm, magnetic stirring bar and stopcock adaptor connected to a mercury bubbler was assembled while hot and flushed with a stream of nitrogen. Diisopinocampheylchloroborane ($Ipc_2BCl$) (8.8 g, 27.5 mmol) was transferred into the flask under a nitrogen atmosphere in a glove bag. While stirring, 3,3-dimethyl-2-butanone (3.3 mL, 25 mmol) was added via a syringe. $Ipc_2BCl$ goes into solution within a few hours. The reaction mixture was quenched with methanol and followed by $^{11}B$ NMR spectroscopy for the completion of the reaction. When the reaction was complete (12 days), the α-pinene formed during the reaction was removed under reduced pressure (0.1 mm Hg, 8 h). The residue was dissolved in $Et_2O$ (50 mL) and diethanolamine (2.2 g) was added. The separated solid was filtered off after 2 h and washed with pentane and the combined filtrate was concentrated by distilling the volatiles. The residual liquid was distilled at 117°-119° C., giving 1.28 g (50% yield) of 3,3-dimethyl-2-butanol, $[\alpha]_D$ +7.53° (neat) after purification by preparative gas liquid chromatography on Carbowax 20M polyethylene glycol (Union Carbide): 93% ee based on $[\alpha]_D$ 8.1° (neat) for the maximum reported rotation. Gas chromatography analysis of its menthyl chloroformate derivative made from (−)-menthyl chloroformate (Aldrich Chemical Company) on Supelcowax glass capillary column (15M) showed a composition of 97.5% S+2.5% R (i.e., 95% ee).

EXAMPLE 10

Reduction of Acetophenone with Ipc$_2$BCl

Under a nitrogen atmosphere, with stirring, acetophenone (3.05 mL, 26 mmol) was added to a solution of diisopinocampheylchloroborane (9.0 g, 28 mmol) in THF (20 mL) at −25° C. A yellow color developed immediately. The reaction was complete after 7 h at −25° C. (followed by $^{11}$B NMR after methanolysis of an aliquot). The volatiles were pumped off at aspirator pressure and the α-pinene was removed under reduced pressure (0.1 mm Hg, 8 h). The residue was dissolved in ethyl ether (100 mL) and diethanolamine (2.2 equiv) was added. The separated solid was filtered off after 2 h and washed twice with pentane (∼30 mL). The combined ether and pentane filtrates were concentrated. The residue, upon distillation (bp 118° C., 22 mm Hg) provided [S]-1-phenylethanol (2.3 g, 72% yield) $[\alpha]^{20}_D$ −42.6° (neat) after purification by preparative gas liquid chromatography on Carbowax 20M; 98% ee based on −43.5° for maximum reported rotation. Gas chromatography analysis of its α-methoxy-α-(trifluoromethyl)phenylacetate (made from (+)-MTPA chloride, Aldrich) on Supelcowax glass capillary column (15m) showed a composition of 98.7% S+1.3% (i.e., 97.4% ee), in good agreement with the optical rotation measurement.

EXAMPLE 11

Reduction of Acetophenone With Ipc$_2$BBr

The reduction of acetophenone with diisopinocampheylbromoborane was carried out under similar conditions as used for the reduction with the corresponding chloroborane (Example 10). Under nitrogen and stirring, acetophenone (2.91 mL, 25 mmol) was added to a solution of Ipc$_2$BBr (10.4 g, 28.6 mmol) in ethyl ether (22 mL) at −25° C. The reaction was followed by $^{11}$B NMR after methanolysis at −25° C. and was complete within 15 h. α-Pinene was removed using a high vacuum pump. Workup using diethanolamine (2.2 g) yielded, on distillation, 2.12 g (70%) of the alcohol which was further purified by preparative gas chromatography on Carbowax 20M. $[\alpha]^{26}_D$ −42.5°; 98%ee based on $[\alpha]_D$ −43.5° for maximum reported rotation.

EXAMPLE 12

Reduction of 3-Methyl-2-butanone with IpcBCl$_2$

Under nitrogen, 3-methyl-2-butanone (2.67 mL, 25 mmol) was added with stirring to a solution of IpcBCl$_2$ (5.5 mL, 27.5 mmol) in CH$_2$Cl$_2$ (16.5 mL) at −25° C. The reaction was followed by $^{11}$B NMR after methanolysis at −25° C. and was complete in 5 h. α-Pinene was pumped off at high vacuum. Ether (50 mL) was added to the reaction flask followed by triethanolamine (12.5 mL, 3.3 eq.). The separated solid, triethanolamine borate, was filtered off, washed with pentane (2×25 mL) and the combined filtrates concentrated by distilling off the volatiles. The alcohol was collected at 110°-112° C. The yield was 1.4 g (63%): $[\alpha]_D$ +2.29., i.e., 42.9% ee based on the maximum value reported in the literature, $[\alpha]_D$ +5.34°. The optical purity of the alcohol was confirmed by an MTPA ester analysis on Supelcowax glass capillary column (15M) which showed 71.5% S isomer and 28.5% R isomer, thus projecting an ee of 43% in S(+).

EXAMPLES 13-20

The chiral reduction of representative aromatic ketones with diisopinocampheylchloroborane in THF at −25° C. was carried out and the results summarized in Table 2 below. Where available, literature values for prior art reagents set out by way of comparison.

TABLE 2

Reduction of Aromatic Ketones with Ipc$_2$BCl(1).
R-Alpine-Borane neat(2), R-Alpine-Borane with high pressure(3) and Binal-H (4)

| Ketone | Reactn. Time (h) | Yield % | $[\alpha]^{20}$D, deg. | % ee Ipc$_2$BCl |
|---|---|---|---|---|
| acetophenone | 7 | 72 | −42.6 | 98$^e$, (97.4)$^f$ |
| 2'-acetonapthone | 7 | 90 | −41.1(c,6.03,EtOH) | 98$^g$ |
| 3-acetylpyridine | 15 | 65 | −43.2(c,1.86,MeOH) | 92$^i$ (92) |
| 2-acetylthiophene | 15 | 85 | −22.5(c,4.41,C$_6$H$_6$) | 91 |
| butyrophenone | 7 | 78 | −45.6(c,4.59,C$_6$H$_6$) | 100.9$^j$ (98) |
| 1-indanone | 15 | 65 | | (97) |
| isobutryophenone | 24 | 68 | −19.2 (neat) | 78$^k$ |
| pivalophenone | 12 days$^l$ | 45 | +20.5(c,1.9,C$_6$H$_6$) | 79$^{m,n}$ |

| Ketone | % ee (2)b | % ee (3)c | % ee (4)$^d$ |
|---|---|---|---|
| acetophenone | 85 | 100 | 95 |
| 2'-acetonapthone | | | |
| 3-acetylpyridine | 90 | 100 | |
| 2-acetylthiophene | | | |
| butyrophenone | | | 100 |
| 1-indanone | | | |
| isobutryophenone | | | 71 |

TABLE 2-continued

Reduction of Aromatic Ketones with Ipc$_2$BCl(1),
R-Alpine-Borane neat(2), R-Alpine-Borane with high
pressure(3) and Binal-H (4)

| pivalophenone | 44 |
|---|---|

[a]Major isomer is the S alcohol.
[b]From Brown et al., J. Org. Chem., 50, 1384 (1985).
[c]From Midland et al., J. Org. Chem., 49, 1317 (1984).
[d]From Noyori et al., J. Am. Chem. Soc., 106, 6709, 6717 (1984).
[e]Based on −43.5° (neat), MacLeod et al., J. Am. Chem. Soc., 82, 876 (1960).
[f]Values in parenthesis are by capillary GC analyses of the (+)-α-methoxy-α-(trifluoromethyl)phenylacetates.
[g]Based on 41.9° (c 4.92, EtOH), Collier et al. J. Chem. Soc., 676 (1940).
[h]Employs 100% excess of the reagent; reaction too slow with stoichimetric amount of the reagent, presumably due to complex formation.
[i]Based on +46.7° for 99% ee alcohol, Uskovic et al., J. Am. Chem. Soc., 101, 6742 (1979).
[j]Based on −45.2° C. (c, 4.81, C$_6$H$_6$).
[k]Based on −24.6° neat, Nasipuri et al., J. Indian Chem. Soc., 44, 165 (1967).
[l]Only 60% reaction is complete after 12 days at room temperature.
[m]Based on 25.9° (c 2.2, C$_6$H$_6$), Vigneron et al, Tetrahedron, 32, 939 (1976).
[n](+) Isomer has R configuration, Clark et al., J. Org. Chem., 35, 1114 (1970).

EXAMPLES 21-24

A comparison of the chiral induction obtained by Ipc$_2$BCl in THF at −25° C. (1), and the values reported in the literature for the leading prior art reagents, Alpine-Borane at 25° C. (2) and under high pressure (3), Binal-H at −100° C. (4) and NB-Enantride at −100° C. (5) are set forth in Table 3.

TABLE 3

A comparison of Chiral Induction Obtained by Various Reagents in the Reduction of Representative Prochiral Ketones

| Ketone | (1) | (2)[a] | (3)[b] | (4)[c] | (5)[d] |
|---|---|---|---|---|---|
| 2-butanone | 4 | 43 | (63)[e] | (24)[e] | 76. |
| 3-methyl-2-butanone | 32 | 62 | 90 | [f] | 68 |
| 3,3-dimethyl-2-butanone | 95[g] | 0.6 | | [h] | 2 |
| acetophenone | 98 | 85 | 100 | 95 | 70 |

[a]From Midland et al., J. Org. Chem., 49, 1317 (1984).
[b]From Brown et al., J. Org. Chem., 50, 1384 (1985).
[c]From Noyori et al., J. Am. Chem. Soc., 106, 6709, 6717 (1984).
[d]From Midland et al., J. Org. Chem., 47, 2496 (1982).
[e]Value for 2-octanone.
[f]Data not available.
[g]At room temperature.
[h]Inert to the reagent.

EXAMPLES 25-31

Following the procedures described above, asymmetric reduction of representative α-tertiary alkyl ketones were carried out with Ipc$_2$BCl (neat) at 25° C. The results are summarized in Table 4 below.

TABLE 4

Asymmetric Reduction of Representative α-Tertiary Alkyl Ketones with Ipc$_2$BCl (neat) at 25° C.

| Ketone (Config.) | Reaction time | Yield % | $[\alpha]^{20}$D.deg. | % ee[a] |
|---|---|---|---|---|
| 3,3-dimethyl-2-butanone (S) | 12 d | 50 | +7.53° (neat) | 93[b](95)[c] |
| ethyl 2,2-dimethylacetoacetate (S)[d] | 12 d | 69 | +3.43° (neat), 1 = 0.05 | (84)[c] |
| 2,2-dimethylcyclopentanone (S)[f] | 12 h | 71 | −24.2° (c, 5.64, C$_6$H$_6$) | (98)[c] |
| 2,2-dimethylcyclohexanone (S)[f] | 12 h | 60 | | (91)[c] |
| spiro[4.4]nonan-1-one (S) | 12 h | 65 | −40.53° (c,0.6, C$_6$H$_6$) | 100[g] (95)[c] |
| methyl 1-methyl-2-oxo-cyclopentane carboxylate[h] | 5 h 60 h(−25°) | | +31.2° (c,2.62, C$_6$H$_6$) | (93)[c] (96)[c] |
| 1-methyl-2-norbornanone (1S,2S) | 15 h | | | (89)[e] |

[a]Values in parentheses are by capillary GC analyses.
[b]Based on 8.1° (neat) (Newman, P., J. Am. Chem. Soc., 80, 465 (1958).
[c]Analysis of the (+)-α-methoxy-α-(trifluoromethyl)phenyl acetate.
[d]Hoffman, R. W. et al., Chem. Ber., 114, 2786 (1981).
[e]Analysis of the (−)-menthylchloroformate derivative.
[f]Based on analogy with the reduction of spiro[4.4]nonan-1-one by Ipc$_2$BCl.
[g]Based on +39.8° (c 1.5, C$_6$H$_6$). (Nakazaki, M. et al., J. Org. Chem., 46, 1147 (1981).
[h]Since the tertiary center was optically active, one-half equivalent of the reagent was used to reduce the more reactive isomer.
[i]Absolute configuration not yet assigned.
[j]Reaction carried out in THF, 1 M.

EXAMPLES 32-40

The chiral induction obtained by Ipc$_2$BCl was compared with the reported values for prior art reagents in the reduction of 3,3-dimethyl-2-butanone. The results are summarized in Table 5.

TABLE 5

A Comparison of Chiral Induction Obtained By Various Reagents in the Reduction of 3,3-Dimethyl-2-butanone

| Reagent | Reaction Condition | % ee |
|---|---|---|
| Ipc$_2$BCl | neat, rt, 12 d | 95 |
| Alpine-Borane | neat, rt, 40 d | 0.6[a] |
| Alpine-Borane | neat, 6 kbar, 9 d. | inert[b] |
| Binal-H | THF, −100° C. | inert[c] |
| NB-Enantride | −100° C., THF/Et$_2$O/Pentane | 2[d] |
| aminoalcohol borane[f] | THF, 0° C. | 96 |

TABLE 5-continued

A Comparison of Chiral Induction Obtained By Various
Reagents in the Reduction of 3,3-Dimethyl-2-butanone

| Reagent | Reaction Condition | % ee |
|---|---|---|
| aminoalcohol borane[f] | THF, −78° C. | -86 |

[a]Noyori, R. et al., J. Am. Chem. Soc., 106, 6709, 6717 (1984).
[b]Brown, H. C., et al., J. Org. Chem., 50, 1384 (1985).
[c]Chandrasekharan, J., et al., J. Org. Chem., 50, 5446 (1985).
[d]Midland, M. M. et al., J. Org. Chem., 47, 2495 (1982).
[f]Amino alcohol prepared by treating the ester of isoleucine with excess phenyl magnesium bromide. Amino alcohol:borane ration was 1:2. Itsuno, S., et al., S. J. Chem. Soc. Perkin Trans. I., 2039 (1985).

As can be seen from the above data, the preferred haloborane of the present invention has definite advantages as a chiral reducing agent for aromatic ketones. As can be seen from Table 5, it is more efficient than Noyori's Binal-H and Midland's Alpine-Borane (without high pressure) and is close to Apline-Borane with high pressure. Further, it employs a far more available chiral auxilliary than Noyori's reagent, permitting large-scale reactions. In addition, the reduction rates are rapidly convenient.

The compounds of the present invention are also superior to most of the prior art agents for the reduction of prochiral α-tertiary ketones. Only Itsuno's isoleucine derived borane reagent may be comparable, however, the generality of that reagent for such reductions has yet to be demonstrated.

The abundant availability of both forms of α-pinene, the simple preparative procedure for the haloborane reagents of this invention, coupled with the simple operating conditions (room temperature, neat) and the easy workup provides numerous advantages over the prior art.

The invention claimed is:

1. A chemically pure diisopinocampheylhaloborane of essentially 100% ee represented by the formula:

$$Ipc_2BX$$

wherein Ipc is isopinocampheyl, B is boron and X is halo.

2. A compound of claim 1, chemically pure diisopinocampheylchloroborane of essentially 100% ee.

3. A compound of claim 1, chemically pure diisopinocampheylbromoborane of essentially 100% ee.

4. A compound of claim 1, chemically pure diisopinocampheyliodoborane of essentially 100% ee.

5. A compound of claim 1, chemically pure diisopinocampheylfluoroborane of essentially 100% ee.

* * * * *